(12) United States Patent
Ding et al.

(10) Patent No.: US 10,213,363 B2
(45) Date of Patent: Feb. 26, 2019

(54) ACUPUNCTURE NEEDLES WITH ACCESSORIES FOR SENSING AND STIMULATION

(71) Applicant: Acumedical, Inc., North Oaks, MN (US)

(72) Inventors: Jiang Ding, Shoreview, MN (US); Lei Chen, North Oaks, MN (US); Jie Xia, Shoreview, MN (US)

(73) Assignee: Acumedical, Inc., North Oaks, MN (US)

( * ) Notice: Subject to any disclaimer, the term of this patent is extended or adjusted under 35 U.S.C. 154(b) by 0 days.

(21) Appl. No.: 15/270,779

(22) Filed: Sep. 20, 2016

(65) Prior Publication Data
US 2018/0055730 A1 Mar. 1, 2018

Related U.S. Application Data

(60) Provisional application No. 62/381,912, filed on Aug. 31, 2016.

(51) Int. Cl.
| | |
|---|---|
| *A61H 39/08* | (2006.01) |
| *A61H 39/00* | (2006.01) |
| *A61H 39/02* | (2006.01) |
| *A61N 1/18* | (2006.01) |
| *A61B 5/053* | (2006.01) |
| *A61B 5/00* | (2006.01) |

(52) U.S. Cl.
CPC ......... *A61H 39/086* (2013.01); *A61B 5/0532* (2013.01); *A61B 5/4854* (2013.01); *A61H 39/002* (2013.01); *A61H 39/02* (2013.01); *A61N 1/18* (2013.01); *A61H 2201/501* (2013.01); *A61H 2201/5023* (2013.01); *A61H 2230/00* (2013.01); *A61H 2230/50* (2013.01); *A61H 2230/60* (2013.01)

(58) Field of Classification Search
CPC .... A61H 39/08; A61H 39/083; A61H 39/086; A61H 39/002; A61H 39/02
See application file for complete search history.

(56) References Cited

U.S. PATENT DOCUMENTS

| | | | | |
|---|---|---|---|---|
| 3,859,983 | A * | 1/1975 | Dohring | A61B 5/0532 600/548 |
| 4,262,672 | A * | 4/1981 | Kief | A61H 39/002 606/189 |

(Continued)

OTHER PUBLICATIONS

"U.S. Appl. No. 15/270,754, Response filed Feb. 9, 2018 to Restriction Requirement dated Jan. 24, 2018", 7 pgs.

(Continued)

*Primary Examiner* — Eric D. Bertram
(74) *Attorney, Agent, or Firm* — Schwegman Lundberg & Woessner, P.A.

(57) ABSTRACT

A sensing and monitoring system can use acupuncture needle-based electrodes for sensing signals from a person and/or delivering stimulation to the person. In various embodiments, the electrodes can include partially insulated acupuncture needles. In various embodiments, the electrodes can include partially insulated or non-insulated acupuncture needles and one or more electrodes incorporated into a needle stopper configured as a guiding tube for an acupuncture needle or integrated into an acupuncture needle.

20 Claims, 12 Drawing Sheets

(56) References Cited

U.S. PATENT DOCUMENTS

| | | | | |
|---|---|---|---|---|
| 5,094,242 A * | 3/1992 | Gleason | ............ | A61N 1/36071 |
| | | | | 128/907 |
| 6,549,810 B1 * | 4/2003 | Leonard | ............... | A61N 1/0551 |
| | | | | 607/115 |
| 6,916,329 B1 | 7/2005 | Zhao | | |
| 7,867,225 B2 | 1/2011 | Heim et al. | | |
| 7,867,226 B2 | 1/2011 | Heim et al. | | |
| 2013/0110150 A1 * | 5/2013 | Yoo | ...................... | A61H 39/002 |
| | | | | 606/189 |

OTHER PUBLICATIONS

"U.S. Appl. No. 15/270,754, Restriction Requirement dated Jan. 24, 2018", 7 pgs.

\* cited by examiner

ACUPUNCTURE NEEDLES WITH ACCESSORIES FOR SENSING AND STIMULATION

CLAIM OF PRIORITY

This application claims the benefit of priority under 35 U.S.C. § 119(e) of U.S. Provisional Patent Application Ser. No. 62/381,912, filed on Aug. 31, 2016, which is herein incorporated by reference in its entirety.

CROSS REFERENCE TO RELATED APPLICATION

This application is related to commonly assigned U.S. patent application Ser. No. 15/270,754, entitled "PARTIALLY INSULATED ACUPUNCTURE NEEDLES FOR SENSING AND STIMULATION", filed on Sep. 20, 2016, which is incorporated by reference in its entirety.

TECHNICAL FIELD

This document relates generally to medical devices and more particularly to a system that performs various diagnostic and therapeutic functions including percutaneous sensing and stimulation using acupuncture needle-based electrodes.

BACKGROUND

Acupuncture has been an important component of traditional Chinese medicine and increasingly accepted in Western countries as a form of alternative medicine. This growing acceptance of acupuncture is largely attributed to its therapeutic effects (e.g., effectiveness in pain relief) that can be achieved without substantial discomfort for the patient and difficulty for the practitioner. However, the fundamental theory of acupuncture remains mysterious because it has yet been proven by modern science. The lack of a scientific approach to the practice of acupuncture has prevented common application of acupuncture in many potentially effective areas beyond a few applications such as pain control.

SUMMARY

A sensing and monitoring system can use acupuncture needle-based electrodes for sensing signals from a person and/or delivering stimulation to the person. In various embodiments, the electrodes can include partially insulated acupuncture needles. In various embodiments, the electrodes can include partially insulated or non-insulated acupuncture needles and one or more electrodes incorporated into a needle stopper configured as a guiding tube for an acupuncture needle or integrated into an acupuncture needle.

In one embodiment, an apparatus configured to provide an interface between a medical device and a person may include an acupuncture needle and a guiding tube. The acupuncture needle may be configured to be connected to the medical device, and may include a handle and a needle body coupled to the handle. The needle body includes a proximal end portion connected to the handle, a distal end portion including a needle tip suitable for piercing the skin and the tissue, and an elongate body shaft coupled between the proximal end portion and the distal end portion. The guiding tube may be configured to assist percutaneous insertion of a substantial portion of the needle body into the tissue of the person, and may include a proximal end including a proximal opening, a distal end including a distal opening for contacting skin, a lumen between the proximal opening and the distal opening, the lumen configured to allow the needle tip to enter the proximal opening and exit from the distal opening, an electrode incorporated into the distal end, and a connector configured to allow for electrical connection between the electrode and the medical device.

In one embodiment, an apparatus configured to provide an interface between a medical device and a person may include an acupuncture needle configured to be connected to the medical device. The acupuncture needle may include a handle, a needle body coupled to the handle, a disk coupled between the handle and the needle body, and an electrode. The needle body may include a proximal end portion connected to the handle, a distal end portion including a needle tip suitable for piercing the skin and the tissue, and an elongate body shaft coupled between the proximal end portion and the distal end portion. The disk may be coupled between the handle and the needle body and approximately perpendicular to the handle and the needle body. The disk may including a skin-contact surface configured to be in contact with the skin of the person when a portion of the needle body is inserted into the tissue of the person such that the needle tip is at an intended depth. The electrode may be incorporated onto the skin-contact surface of the disk.

In one embodiment, a method for providing an interface between a medical device and a person is provided. The method may include providing an acupuncture needle including a handle and a needle body coupled to the handle. The needle body may include a proximal end portion connected to the handle, a distal end portion including a needle tip, and an elongate body shaft coupled between the proximal end portion and the distal end portion. The handle and the needle body may be substantially bendable and have sufficient stiffness for percutaneous insertion of a substantial portion of the needle body into the tissue by applying force using the handle. The needle tip may be shaped and sized to pierce the skin and the tissue. The method may further include providing a needle stopper configured to stop the needle tip from further penetration into the tissue when an intended depth is reached. The needle stopper may include a skin-contact surface that contacts the skin when the needle tip is at the intended depth. The method may further include incorporating an electrode onto the skin-contact surface, providing a first electrical connection between the needle body and the medical device, and providing a second electrical connection between the electrode and the medical device.

This summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

Figure 1:
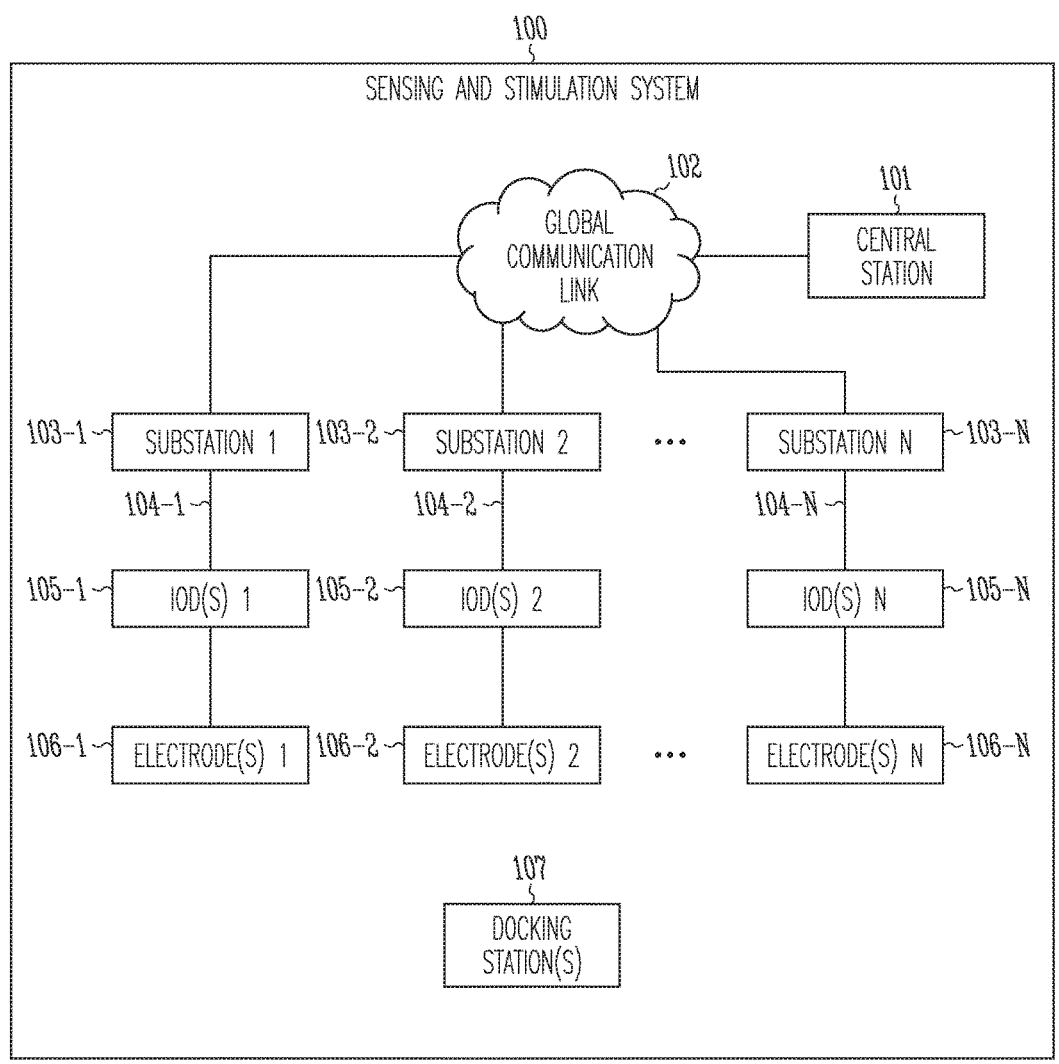
FIG. 1 is a block diagram illustrating an embodiment of a sensing and stimulation system.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

This document discusses, among other things, methods and apparatuses for performing various medical diagnostic and/or therapeutic functions by incorporating modern technologies in acupuncture and/or applying various aspects of acupuncture in medical electronic devices.

The original acupuncture concept was based on the view of traditional Chinese medicine and philosophy that forces of "yin" and "yang" exist everywhere in the nature, where every natural phenomenon, including biological phenomenon, results from their constant interactions. Yin (dark) represents feminine, passive, or accepting qualities, while yang (bright) represents masculine, aggressive, or forceful qualities. In a human body, a vital energy of "qi" (circulating life force) flows through a complex network known as the meridian system (also referred to as "meridian network" or "channel network") to regulate the balance of yin and yang. Insufficient, unbalanced, interrupted, or otherwise abnormal flow of qi causes imbalance of yin and yang and hence pathological conditions.

The purpose of acupuncture is to intervene at specific body sites known as "acupuncture points" (also referred to as "acupoints") in the meridian system to adjust qi and rebalance the yin and yang. To perform acupuncture, a practitioner inserts one or more elongate metal needles percutaneously into one or more specifically selected acupoints. In many examples, multiple needles are used at a number of specific acupoints. Whe advancing each needle to a desired depth, the practitioner skillfully maneuvers the needle by turning, shaking, and pulsing, among other movements. Such manual maneuver (referred to as "yun zhen") is a crucial part of an acupuncture therapy. Different abnormal conditions require different maneuvers for therapeutic effectiveness. Thus, the ability of executing such maneuvers at least partially determines the level of skill of an acupuncture therapist, and limits the number of acupuncture therapists who can acquire skills required to apply many complicated acupuncture therapies that require very precise maneuvers for safety and/or efficacy.

Having been mapped based on experience over many centuries, the meridian system and the acupuncture points have not been identified as anatomical features or being associated in some way to known anatomical features (such as the nervous system or circulatory system). Thus, in addition to the manual maneuver, the ability of accurately locating various acupoints also determines the level of skill of the acupuncture therapist and limits the number of acupuncture therapists who can acquire skills required to apply many complicated acupuncture therapies that require very previse locations for safety and/or efficacy.

Because acupuncture needles are made of metal, electrical currents have been introduced into tissue through the needles to stimulate the tissue to supplement, enhance, or replace the manual maneuvers, a practice known as electro-acupuncture. Examples of benefits of electro-acupuncture, or electrical stimulation using acupuncture needles, may include, but are not limited to: (1) replacing manual maneuvers of the acupuncture needles: electro-acupuncture can be applied to avoid prolonged manual maneuvering (which may become less accurate and less effective with hand fatigue), and can relieve the strict requirements of training for hand manipulation, thereby enabling a novice practitioner to achieve the same or comparable effects of needle maneuvers by an experienced practitioner; (2) providing longer stimulation duration to achieve desired therapeutic effects: electrical stimulation can be turned on for an entire therapy session, during which the practitioner can attend to other patients, thereby increasing the number of patients treated by the practitioner and/or the therapy duration available for each patient; (3) providing a stronger stimulation without causing tissue damage associated with twirling, lifting and thrusting the acupuncture needles, such as when high intensity stimulation is needed for difficult cases such as neuralgia or paralysis; and (4) facilitating the applications: controlling parameters of electrical stimulation is easier than performing the manual maneuvers of the acupuncture needles, especially with the modern electronics technology.

Such benefits are limited, however, at least in part by the lacking of scientific knowledge on acupuncture in general. For example, stimulation sites for electro-acupuncture still need to be manually located, and ability for programming parameters for electrical stimulation is limited by lacking of scientific understanding of how the human body responds to various maneuvers of acupuncture needles by the practitioner's hand.

The present subject matter provides a multi-point stimulation and data collection system for medical applications. In various embodiments, the system can use modern technologies to facilitate, assist, supplement, enhance, and/or replace various aspects of traditional acupuncture therapy. In various embodiments, the system can perform diagnostic and/or therapeutic functions using components developed by at least partially using acupunctural concepts, techniques, and/or devices. In various embodiments, the system can include a central station, one or more substations, and one or more input/output devices (IODs). The central station is remotely connected to at least one of the substations via a communication link. Each substation is locally or remotely connected to at least one IOD. Each IOD is physically and electrically connected to at least electrode of any type and shape (e.g., needle or patch). The electrode is attached onto or inserted into the skin of a patient. In various embodiments, the system can operate in a clinical environment where multi-point stimulation on or under the skin is performed for diagnosis of or therapy for certain medical conditions. Under guidance of a pre-designed study protocol, the system can collect data and deliver stimuli through electrodes. The data collection and stimulation delivery can be executed manually, automatically, or semi-automatically based on specific design of the diagnosis and/or theraoy protocol. During a diagnosis and/or therapy session, the system can monitor the progress of the diagnosis and/or therapy in real-time, and can organize, classify, and store the collected data for post-study analysis.

In this document, a "user" can include a trained professional, such as a physician or other caregiver, who uses the methods and apparatuses discussed in this document to treat one or more patients. A "patient" can include any person from whom one or more signals are sensed, and/or to whom one or more therapies are delivered, using the methods and apparatuses discussed in this document. The patient may be a person seeking medical help and/or participating in a clinical study. A "person" can refer to such a patient.

FIG. 1 is a block diagram illustrating an embodiment of a sensing and stimulation system 100. System 100 can include a central station 101, a global communication link 102, one or more substations 103, one or more local communication links 104, one or more input/output devices (IODs) 105, electrodes 106, and one or more docking stations 107. An example of central station 101 is further discussed below with reference to FIG. 2.

In various embodiments, global communication link 102 can include a wireless communication network and/or a wired communication network. Examples of global communication link 102 include the Internet, an intranet, and a cellular network.

Substation(s) 103 can include one or more substations each communicatively coupled to central station 101 via global communication link 102. While a plurality of substations 103-1, 103-2, . . . and 103-N are illustrated in FIG. 1, various embodiments can include any number of substations, subjected to the capability of central station 101 (i.e., N=1, 2, 3, . . . ). An example for one of substation(s) 103 is further discussed below with reference to FIG. 3.

Local communication link(s) 104 can each include a wired communication link or a wireless communication link coupled between one of substation(s) 103 and one of IOD(s) 105. Examples of the wired communication link include a cable such as a USB cable or Ethernet cable. Examples of the wireless communication link includes a Bluetooth® link, a Bluetooth low energy (BLE) link, an IEEE 802.11 (wireless LANs) link, an 802.15 (WPANs) link, an 802.16 (Wi-MAX) link, an electromagnetic communication link (e.g., an RF far-field or inductive link), an optical communication link (e.g., an infrared link), an acoustic communication link (such as an ultrasound link) and a cellular communication link (e.g., CDMA, GSM, ZigBee, or Ultra-wideband (UWB) link).

IOD(s) 105 can each be communicatively coupled to one of substation(s) 103 via one of local communication link(s) 104. In FIG. 1, each of IOD(s) 105-1, 105-2, . . . and 105-N represent a set of one or more IODs communicatively coupled to one of substations 103-1, 103-2, . . . and 103-N via one of more local communication links 104-1, 104-2, . . . and 104-N, respectively. An example for one of IOD(s) 105 is further discussed below with reference to FIG. 4.

Electrodes 106 provide for an interface between system 100 and one or more patients being diagnosed, monitored, and/or treated using system 100. In FIG. 1, each of electrode(s) 106-1, 106-2, . . . and 106-N represent a set of one or more electrodes electrically connected to IOD(s) 105-1, 105-2, . . . and 105-N, respectively. Each IOD functions as a front-end device that is connected to a patient via one or more electrodes. Examples of electrodes 106 can include surface electrodes (e.g., skin patch electrodes, transcutaneous electrical nerve stimulation (TENS) electrodes, and surface neuromuscular sensing electrodes) and percutaneous electrodes (e.g., needle electrodes). Examples of needle electrodes are further discussed below with reference to FIGS. 6-14.

Docking station(s) 107 each allow one or more IODs 105 to dock and recharged. An example for one of docking station(s) 107 is further discussed below with reference to FIG. 5.

In various embodiments, circuits of system 100, including its various embodiments discussed in this document, may be implemented using a combination of hardware and software. For example, portions of various communication circuits, encoding and decoding circuits, circuits of user interfaces, positioning circuits, and control circuits, as discussed below in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 2:
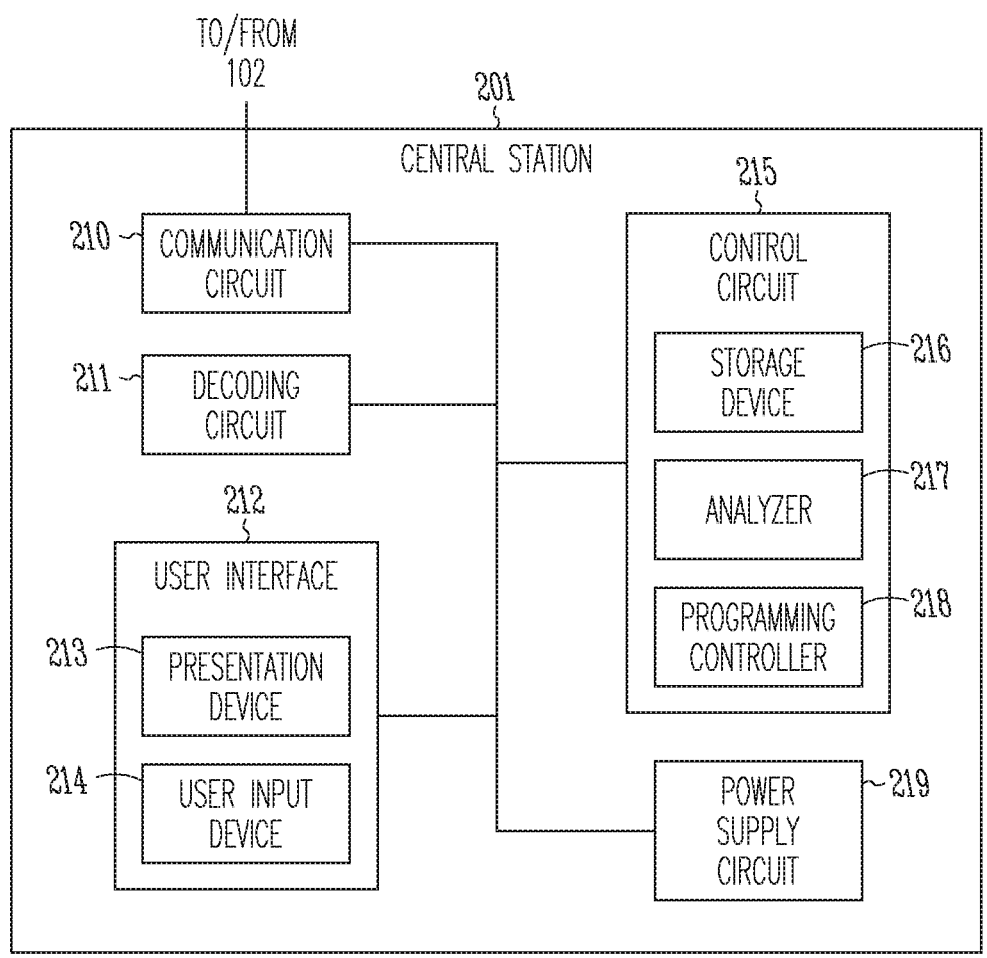
FIG. 2 is a block diagram illustrating an embodiment of a central station of the monitoring and stimulation system.

FIG. 2 is a block diagram illustrating an embodiment of a central station 201, which represents an example of central station 101. Central station 201 can include a communication circuit 210, a decoding circuit 211, a user interface 212, a control circuit 215, and a power supply circuit 219. In various embodiments, central station 201 can be implemented on a generic computer and/or as a custom-made device.

Communication circuit 210 can communicate with each substation of substation(s) 103 via global communication link 102. In various embodiments, communication circuit 210 can receive data from each substation of substation(s) 103. The data can be acquired by the substation and include data indicative of operation status of the substation and operation status of each IOD of IOD(s) 105 communicatively coupled to that substation. In one embodiment, the data can be received by communication circuit 210 in real time. In some embodiments, central station 201 only monitors substation(s) 103 and perform analyses of the data acquired by substation(s) 103, such as for statistical studies. In other embodiments, central station 201 can also be used to control the operation of substation(s) 103 and/or IOD(s) 105.

Decoding circuit 211 can identify each substation of substation(s) 103 that is connected to central station 201 via global communication link 102 using a unique substation identification code assigned to that substation. In various embodiments, the identification code can indicate the owner or user, the patient, the location, etc., associated with the substation identified by the identification code.

User interface 212 can include a presentation device 213 to present information received from each substation and a user input device 214 to receive commands and other information from the user. In various embodiments, user interface 212 can include a graphic user interface (GUI). In various embodiments, portions of presentation device 213 and user input device 214 can be integrated into an interactive touchscreen. In various embodiments, presentation device 213 can include any type of presentation device, such as interactive or non-interactive screens. Use input device 214 can include any type of user input devices, such as touchscreen, keyboard, keypad, touchpad, trackball, joystick, and mouse.

Control circuit 215 controls operation of central station 201. Control circuit 215 can include a storage device 216, an analyzer 217, and a programming controller 218. Storage device 216 can store data received from substation(s) 103 and results of analysis performed by central station 201. Analyzer 217 analyzes the data received from each substation of substation(s) 103. In various embodiments, the analysis performed by analyzer 217 can include detection of specified type information from the data received from each substation. Examples of such specified type information include the number of IOD(s) 105 communicatively coupled to the substation, a current operation mode of each IOD communicatively coupled to the substation (e.g., a sensing mode and a stimulation mode), an operation status of each IOD communicatively coupled to the substation (e.g., normal function and abnormal function), and/or the battery levels of the substation and/or each IOD communicatively coupled to the substation. In various embodiments, analyzer 217 can generate one or more reports based on the analysis. In various embodiments, analyzer 217 can organize and/or classify the reports, selectively store one or more of the reports in storage device 216, and/or selectively present one or more of the reports using presentation device 213. In various embodiments, analyzer 217 can organize and/or classify the reports, selectively store one or more of the reports in storage device 216, and/or selectively present one or more of the reports using presentation device 213 according to specified criteria. The specified criteria can include predetermined criteria and/or user-selected criteria received using user input device 214. Programming controller 218 allows the user to adjust the operation of central station 201 and/or various other portions of system 100, such as using user interface 212. In embodiments in which central station 201 can be used to control the operation of substation(s) 103 and/or IOD(s) 105, programming controller 218 can generate programming codes to be transmitted to one or more of substation(s) 103 and/or IOD(s) 105 to be programmed or reprogrammed via global communication link 102. Programming controller 218 can generate programming codes based on predetermined programming instructions stored in storage device 216, user commands received using user input device 214, outcome of the analysis performed by analyzer 217, the operation status of each of substation(s) 103, and/or the operation status of each of IOD(s) 105. Power supply circuit 219 provides power for the operation of central station 201.

Figure 3:
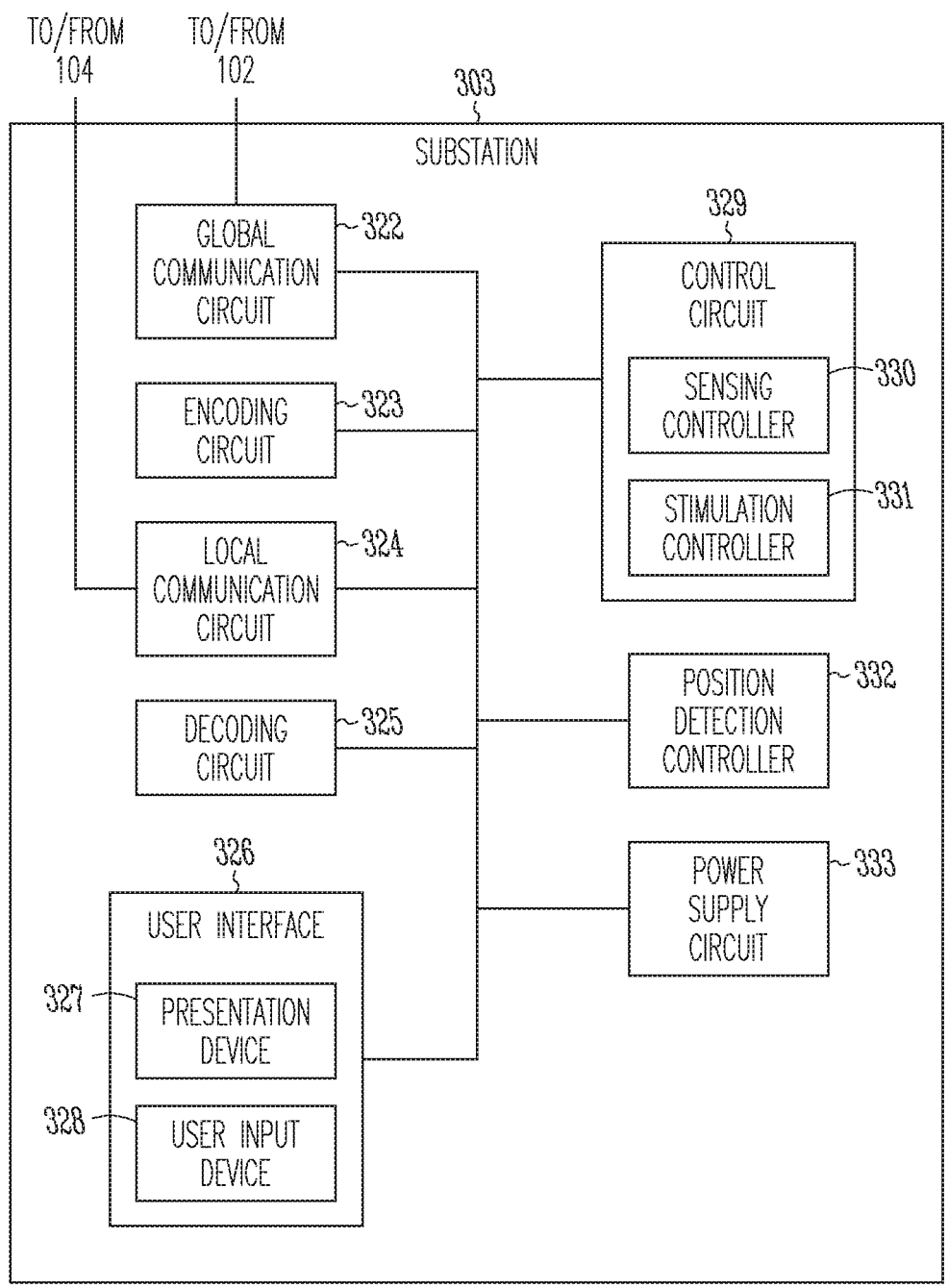
FIG. 3 is a block diagram illustrating an embodiment of a substation of the monitoring and stimulation system.

FIG. 3 is a block diagram illustrating an embodiment of a substation 303, which represents an example of one of substation(s) 103. Substation 303 can include a global communication circuit 322, an encoding circuit 323, a local communication circuit 324, a decoding circuit 325, a user interface 326, a control circuit 329, a position detection controller 332, and a power supply circuit 333. In various embodiments, substation 303 can be implemented on a generic computer and/or as a custom-made device.

Global communication circuit 322 can communicate with central station 101 via global communication link 102, including transmitting the data acquired by substation 303 to central station 101. Encoding circuit 323 can generate the unique substation identification code for substation 303. Local communication circuit 324 can communicate with one or more IODs of IOD(s) 105 via one or more local communication links of local communication link(s) 104. In various embodiments, local communication circuit 324 can receive signals from each IOD connected to substation 303 via a link of local communication link(s) 104. Examples of such received signals include one or more physiological signals acquired by the IOD (e.g., a signal indicative of electrical activities in the patient, a signal indicative of a temperature in the patient, and/or a signal indicative of a chemical parameter measured from the patient, such as pH value), one or more status signals indicative of operational status of the IOD (e.g., a current operation mode of the IOD, normal function of the IOD, and/or abnormal function of the IOD), a unique IOD identification code associated with the IOD indicating that IOD is connected, and/or a signal indicative of a strength and/or data transmission quality of the local communication link coupled between the IOD and substation 303. In various embodiments, local communication circuit 324 can also transmit signals to each IOD connected to substation 303 via a link of local communication link(s) 104. Examples of such transmitted signals include signals for controlling operation of the IOD (e.g., sensing parameters and stimulation parameters). Decoding circuit 325 can identify each IOD connected to substation 303 via a link of local communication link(s) 104 by a unique IOD identification code associated with that IOD.

User interface 326 can include a presentation device 327 to present information received from central station 101 and IOD(s) 105 and a user input device 328 to receive commands and other information from the user. In various embodiments, user interface 326 can include a graphic user interface (GUI). In various embodiments, portions of presentation device 327 and user input device 328 can be integrated into an interactive touchscreen. In various embodiments, presentation device 327 can include any type of presentation device, such as interactive or non-interactive screens. Use input device 328 can include any type of user input devices, such as touchscreen, keyboard, keypad, touchpad, trackball, joystick, and mouse. In various embodiments, presentation device 327 can present a graphic or non-graphic representation of a target map. The target map can include, for example, the meridian system including meridians (routes), acupoints, trigger points, neuro-acupuncture points, and/or other specified electrostimulation points on the skin/body surface (cutaneous sites) and/or underneath the skin (subcutaneous sites), location of each electrode of electrodes 106 currently deployed (connected to each IOD of IOD(s) 105 that is connected to substation 303 via a link of local communication link(s) 104), and/or status of each IOD of IOD(s) 105 that is connected to substation 303 via a link of local communication link(s) 104.

Control circuit 329 controls operation of substation 303 and can include a sensing controller 330 and a stimulation controller 331. Sensing controller 330 can process the signals received from each IOD that is connected to substation 303. In various embodiments, sensing controller 330 can generate sensing parameters for controlling sensing functions of the IOD. In various embodiments, sensing controller 330 can analyze the processed signals including organizing the processed signals and classifying the processed signals, selectively store one or more of processed signals in substation 303, selectively present one or more of the processed signals using presentation device 327, and/or selectively transmit one or more of processed signals to central station 101. In various embodiments, sensing controller 330 selective stores one or more of processed signals in substation 303, selectively presents one or more of processed signals using presentation device 327, and/or selectively transmits one or more of processed signals to central station 101 according to specified criteria. The specified criteria can include predetermined criteria and/or criteria received from the user using user input device 328. In various embodiments, sensing controller 330 can detect location of each deployed electrode of electrodes 106 that is connected to substation 303 via an IOD of IOD(s) 105 and a link of local communication link(s) 104 on the target map. In one embodiment, sensing controller 330 receives the location of each electrode manually entered by the user using user input device 328. In another embodiment, sensing controller 330 detects the location of each electrode automatically using positioning detection controller 332, as further discussed below. In various embodiments, sensing controller 330 can detect characteristics of each deployed electrode including, for example, its type, mechanical parameters, and electrical parameters. In one embodiment, sensing controller 330 receives such characteristics from the user manually entering them using user input device 328. In various embodiments, sensing controller 330 can detect a current operation mode of each IOD that is connected to substation 303. Examples of the current operation mode can include standby, sensing, and/or stimulation. In various embodiments, sensing controller 330 can detect a battery level of each IOD that is connected to substation 303. In various embodiments, sensing controller 330 can identify signals sensed by each deployed electrode that is connected to substation 303. In various embodiments, sensing controller 330 can generate sensing parameters instructing one or more IODs connected to substation 303 to sense one or more specified type signals using one or more specified electrodes. In one embodiment, sensing controller 330 generates such sensing parameters after delivery of a stimulus or after a delay period following the delivery of the stimulus.

Stimulation controller 331 can generate stimulation parameters controlling delivery of stimulation from each IOD connected to substation 303. In various embodiments, the stimulation parameters can define a stimulus as a single pulse, a burst of pulses, a sequence of bursts, a continuous waveform, etc. The stimulation parameters can specify a constant or varying (e.g., modulated) pulse frequency and/or a constant or varying (e.g., modulated) pulse amplitude. In various embodiments, stimulation controller 331 can generate the stimulation parameters using the signals processed by sensing controller 330 and/or outcome of the analysis of processed signals performed by sensing controller 330. In various embodiments, stimulation controller 331 can instruct each IOD connected to substation 303 to deliver a stimulus using the outcome of the analysis of processed signals performed by sensing controller 330 and one or more predetermined thresholds. In one embodiment, stimulation controller 331 generates the stimulus and transmits the stimulus to an intended IOD for delivery through one or more specified electrodes connected to the IOD (i.e., the IOD simply relays the stimuli). In another embodiment, stimulation controller 331 generates stimulation parameters and transmits the stimulation parameters to the IOD, which then generates the stimulus and delivers the stimulus through one or more specified electrodes connected to the IOD according to the stimulation parameters.

In various embodiments, control circuit 329 can generate a report for each diagnostic and/or therapeutic session with the patient. The report can include, for example, the patient's demographics (e.g., age and gender), identification and location of each IOD connected to substation 330 on the target map, parameters of the stimuli delivered during the session (e.g., type and duration), and/or notes received from the user using user input device 328 (e.g., observations and comments regarding effects of the delivery of the stimuli).

Position detection controller 332 allows substation 303 to detect location of each IOD connected to substation 303 using triangulation. When a deployed electrode connected to each IOD is directly attached to that IOD or placed in close proximity of that IOD, it allows for detection of approximate location of the deployed electrodes. Automatic detection of IOD locations using triangulation is possible with three or more IODs (referred to as pinning IODs) each having a positioning circuit (as discussed below with reference to FIG. 4) are placed at certain selected areas on the patent and emit the acoustic signals. The time of the emission is controlled by position detection controller 332 and synchronized with the IODs connected to substation 303, such as by transmitting a synchronization mark to each of the connected IODs. In response to instructions of position detection controller 332, each of the connected IODs receives the acoustic signal emitted from the pinning IODs, and measures the time delay between the emission of the acoustic signal from pinning IODs and the reception of the acoustic signal by the IOD. The time delay is reported back to sensing controller 330 and used by position detection controller 332 to determine the location of each IOD relative to the known locations of the pinning IODs using the triangulation method.

Power supply circuit 333 can provide power for the operation of substation 303. In various embodiments, power supply circuit 333 can include a battery, an AC adaptor, or both.

Figure 4:
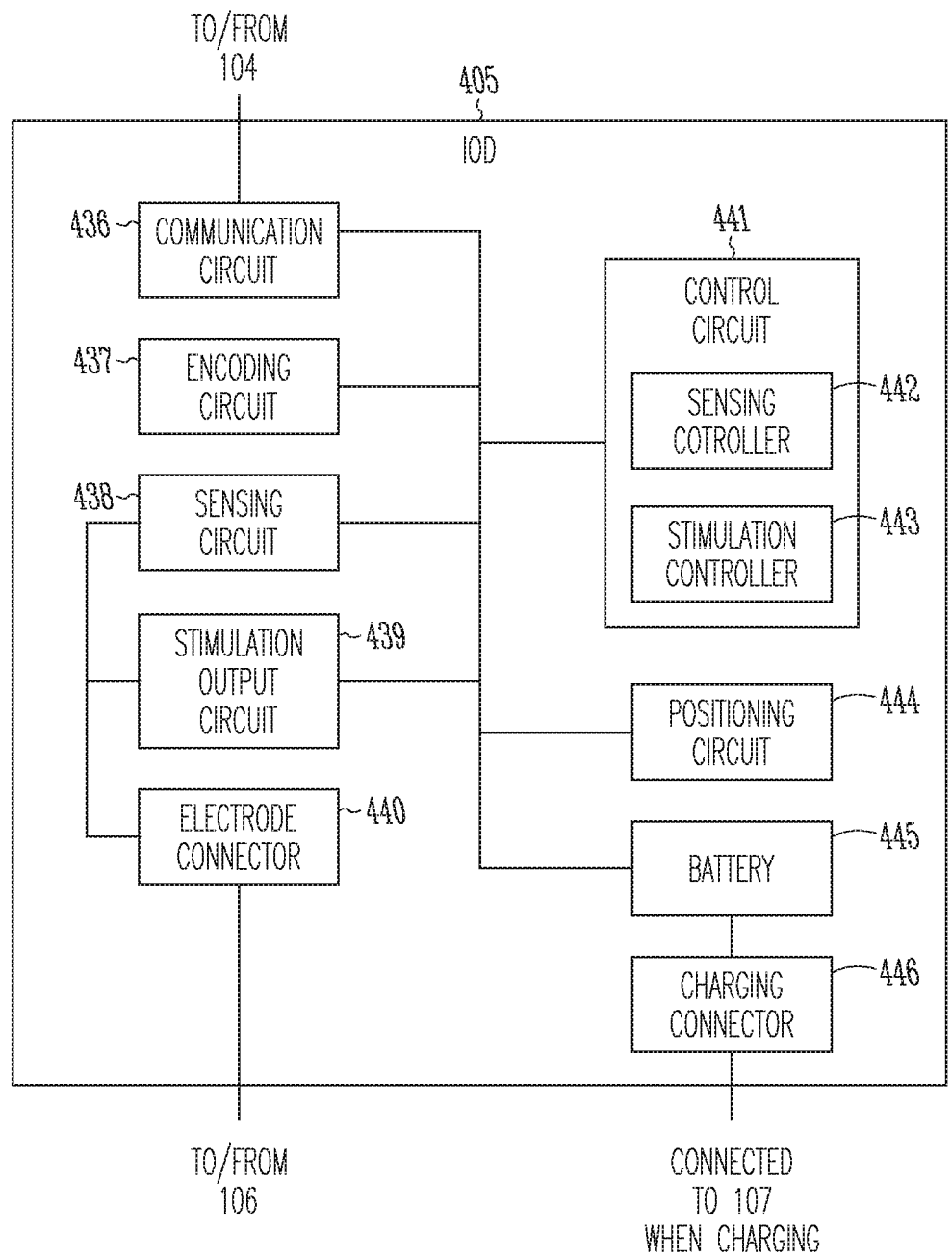
FIG. 4 is a block diagram illustrating an embodiment of an input/output device (IOD) of the monitoring and stimulation system.

FIG. 4 is a block diagram illustrating an embodiment of an IOD 405, which represents an example of one of IOD(s) 105. IOD 405 can include a communication circuit 436, an encoding circuit 437, a sensing circuit 438, a stimulation output circuit 439, an electrode connector 440, a control circuit 441, a positional circuit 444, a battery 445, and a charging connector 446. In various embodiments, IOD 405 can include a chassis housing communication circuit 436, encoding circuit 437, sensing circuit 438, stimulation output circuit 439, control circuit 441, positional circuit 444, and battery 445, while electrode connector 440 and charging connector can be incorporated onto the chassis. In various embodiments, IOD 405 is visually identifiable using an identification feature incorporated onto the chassis. In one embodiment, the unique IOD identification code is visibly labeled or displayed on the IOD chassis.

Communication circuit 436 can communicate with a substation of substation(s) 103 that is connected to IOD 405 via a link the local communication link(s) 104. In various embodiments, communication circuit can receive signals transmitted from the connected substation (e.g., the stimulus or stimulation parameters and/or the sensing parameters) and/or transmit signals to the connected substation (e.g., one or more physiological signals sensed by sensing circuit 438, the one or more status signals indicative of operational status of IOD 405, and/or the unique IOD identification code associated with IOD 405). Encoding circuit 437 can generate the unique IOD identification code for IOD 405.

Sensing circuit 438 can sense one or more physiological signals through one or more electrodes of electrodes 106 that are connected to IOD 405 through electrode connector 440. In various embodiments, sensing circuit 438 can sense one or more physiological signals according to the sensing parameters. Examples of the one or more physiological signals can include neuromuscular signals, signals allowing for characterization of electrical properties of the meridian system, a signal indicative of temperature (through an electrode with an embedded temperature sensor), and/or a signal indicative of pH value and/or other chemical parameters (through an electrode with an embedded chemical sensor).

Stimulation output circuit 439 can deliver the stimuli through one or more electrodes of electrodes 106 that are connected to IOD 405 through electrode connector 440. In various embodiments, the stimuli can include electrical current, such as in the form of pulses. In various embodiments, the stimuli can also include various forms of magnetic, thermal, acoustic, optical, and mechanical energy as well as chemical and biological agents.

Electrode connector 440 allow for physical and electrical connections to the one or more electrodes, directly or through one or more cables or leads. In various embodiments, electrode connector 440 can provide one or more electrical connections between one or more electrodes and sensing circuit 438 and/or one or more electrical connections between one or more electrodes and stimulation output circuit 439. In one embodiment, the one or more electrical connections between one or more electrodes and sensing circuit 438 and the one or more electrical connections between one or more electrodes and stimulation output circuit 439 include one or more common electrical connections.

Control circuit 441 controls operation of IOD 405 and can include a sensing controller 442 and a stimulation controller 443. Sensing controller 442 can control the sensing of the one or more physiological signals using one or more predetermined sensing parameters and/or one or more sensing parameters received from the connected substation. Stimulation controller 443 can control the delivery of the stimuli using the stimulus received from the connected substation or the stimulation parameters received from the connected substation.

Positioning circuit 444 allows for determination of position of IOD 405 relative to one or more known locations on the patient's body using triangulation, and can include one or more acoustic transducers to emit and receive acoustic signals, such as audible or ultrasonic signals. Positioning circuit 444 can receive commands from substation 303 to emit or receive acoustic signals, calculate a time interval between emission of the acoustic signal from another IOD (i.e., a pinning IOD) and the reception of that acoustic signal by IOD 405, and transmit the time interval to the connected substation 303.

Battery 445 can provide energy for operation of IOD 405. In various embodiments, battery 445 includes a rechargeable battery that can be recharged by electrically connecting to a docking station of docking station(s) 107 through charging connector 446. In various embodiments, control circuit 441 can perform battery management functions including detecting a battery status (e.g., an energy level) of battery 445 and transmit the battery status to the connected substation.

Figure 5:
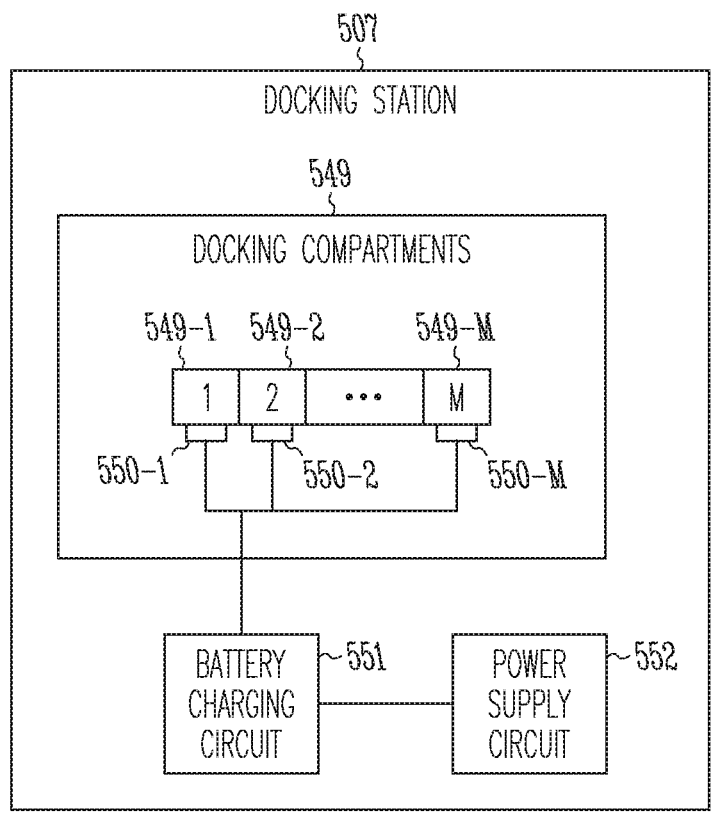
FIG. 5 is a block diagram illustrating an embodiment of a docking station of the monitoring and stimulation system.

FIG. 5 is a block diagram illustrating an embodiment of a docking station 507, which represents an example of one of docking station(s) 107. Docking station 507 can include one or more docking compartments 549 each accommodate an IOD of IOD(s) 105, a battery charge circuit 551, and a power supply circuit 552. In various embodiments, docking compartments 549-1, 549-2, . . . 549-M (M=1, 2, . . . ) can each include a visible identification feature that identifies an IOD of IOD(s) 105 that is intended to be docked in the docking compartment. In one embodiment, docking compartments 549-1, 549-2, . . . and 549-M are each labeled with the unique IOD identification code of the IOD intended to be docked. Docking compartments 549-1, 549-2, . . . and 549-M each have a structure to mate with the IOD chassis of the IOD intended to be docked to securely hold the IOD in place, and include battery charging connectors 550-1, 550-2, . . . and 550-M each connected to battery charging circuit 551 and configured to mate with the charging connector (e.g., charging connector 446) of the docked IOD. Power supply circuit 552 can supply power for operation of docking station 507. Battery charging circuit 551 can receive power from power supply circuit 552 and convert the received power to a form suitable for charging the docked IOD(s).

In an example of application, system 100 works in a clinical environment where surface stimulation and/or percutaneous stimulation are performed. Guided by a pre-designed protocol, the user turns on the power of a substation. After an initialization of the substation (including communication to the connected central station), the user decides where to place electrodes, on the skin or in the tissue under the skin, at various locations based on a specific therapy methodology (e.g., acupuncture therapy, trigger-point therapy, or neurostimulation therapy). Once decided, the user marks the location of each electrode onto a target map (showing the meridian system for example). Alternatively, the substation can localize the electrodes automatically using triangulation. Then, the user places each electrode on the skin or in the tissue according to the decided locations. After turning on the IODs, there is a period of initialization when the substation establishes communication with each IOD. When the therapy session begins, the user enters various commands from the substation to instruct one or more IODs to either record data or deliver specific stimulus according to the pre-designed protocol. The protocol can also be executed by the substation when sensing and stimulation can be controlled automatically. During the therapy session, the user can monitor the progress including the status of each IOD in real-time, and adjust the procedure whenever necessary according to the protocol.

Various embodiments of system 100, central station 201, substation 303, IOD 405, and docking station 507 may not include all the components illustrated in FIGS. 1, 2, 3, 4, and 5, respectively, and may depend on the desired functionality of each system or device for each specific application. For example, position detection controller 332 of substation 303 and positioning circuit 444 of IOD 405 are not needed if automatic detection of IOD/electrode locations using triangulation is not performed, and components providing system 100 with sensing capabilities may not be needed if the system is used in a stimulation-only electro-acupuncture application.

Examples of Electrodes

FIGS. 6-14 illustrate various embodiments of needle electrodes and their use in a medical diagnostic and/or therapeutic system, such as their use as electrode(s) 106 in system 100. The needle electrodes and their accessories, including sizes and shapes of their various features, are illustrated FIGS. 6-14 by way of example, but not by way of restriction.

Figure 6:
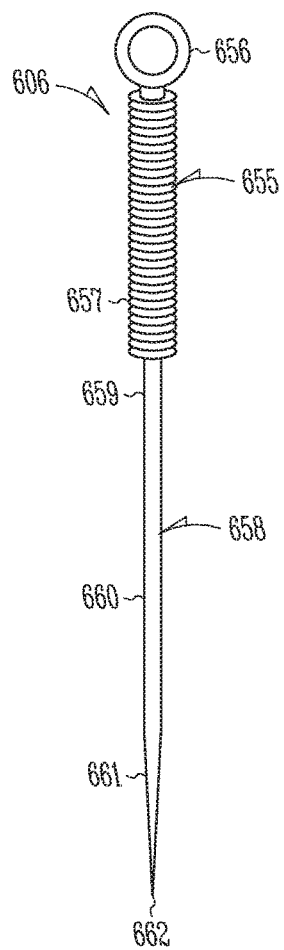
FIG. 6 is an illustration of an embodiment of an acupuncture needle.

FIG. 6 is an illustration of an embodiment of an acupuncture needle 606. Acupuncture needle 606 represents an example of an electrode such as one of electrode(s) 106, and includes a handle 655 and a needle body 658 coupled to handle 655. In various embodiments, needle body 658 can be substantially bendable and has sufficient stiffness for percutaneous insertion into tissue of the patient by applying force to handle 655. In some embodiments, both handle 655 and needle body 658 are substantially bendable.

In various embodiments, handle 655 includes a connector portion electrically coupled to needle body 658 to allow for an electrical connection between needle body 658 and a medical device such as one of IOD(s) 105. In the illustrated embodiment, handle 655 includes a ring top 656 and a handle shaft 657. Handle shaft 657 is coupled between needle body 658 and ring top 656. In various embodiments, handle shaft 657 can include a coiled structure or any other structure suitable for being held by a hand to perform acupuncture maneuvering. Portions of ring top 656 and/or handle shaft 657, wherever not electrically insulated, can be used as the connector portion. In other embodiments, handle 655 can include a connector specifically configured to allow for the electrical connection using a cable or a connector specifically configured to be directly attached to the medical device such as one of IOD(s) 105. In various embodiments, handle 655 can include an identification feature, such as a color. For example, when a plurality of acupuncture needles are used in the same system or for the same patient, their handles can be color codes for identifying different types and/or sizes.

Needle body 658 includes a proximal end portion 659 coupled to handle 655, a distal end portion 661 including a needle tip 662, and an elongate body shaft 660 coupled between proximal end portion 659 and distal end portion 661. Needle tip 662 is shaped and sized to pierce tissue of the patient without causing excessive pain to the patient or breakage of acupuncture needle 606. In various embodiments, the length of needle body 658 (which may be referred to as the length of the acupuncture needle) can be in the range of approximately 13-130 mm, and the diameter of elongate body shaft 660 (which may be referred to as the diameter of the acupuncture needle) is in the range of approximately 0.16-0.46 mm. Acupuncture needle 606 can be made of a metal material such as stainless steel. In some embodiments, acupuncture needle 606 can be gold or silver coated. In some embodiments, handle 655 and needle body 658 can be formed using a single piece of metal wire.

While acupuncture needles are specifically discussed as examples of needle electrodes, various features incorporated into an acupuncture needle, as discussed in this document such as with reference to FIGS. 7-9, 11, and 13, can also be incorporated into other types of needles for use as electrodes such as electrode(s) 106 in system 100. Examples of such other types of needles include biopsy needles and injection needles. In some embodiments, one or more sensors can be embedded in the needle body of a needle electrode, such as a temperature sensor and a chemical sensor.

Figure 7:
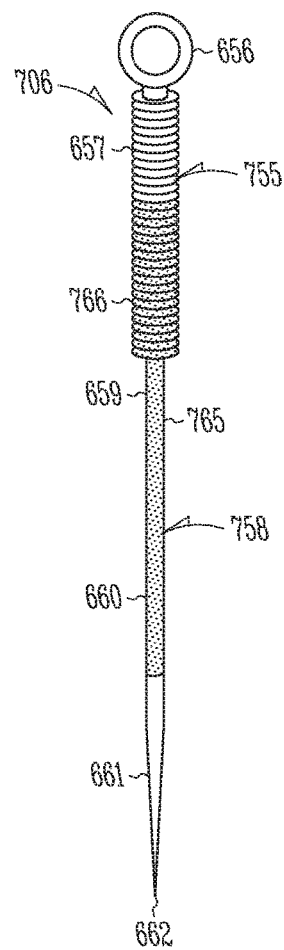
FIG. 7 is an illustration of an embodiment of a partially insulated acupuncture needle.

FIG. 7 is an illustration of an embodiment of a partially insulated acupuncture needle 706, which represents another example of an electrode such as one of electrode(s) 106. Acupuncture needle 706 is substantially identical or similar to acupuncture needle 606 but is partially insulated. In the illustrated embodiment, acupuncture needle 706 includes a handle 755 with an insulation layer 766 and a needle body 758 with an insulation layer 765. In various embodiments, handle 755 can include no insulation layer 766, insulation layer 766 covering about the whole length of handle shaft 657, or insulation layer 766 covering any portion of handle shaft 657. Insulation layer 765 can cover any portion of needle body 758. In various embodiments, insulation layer 765 can have a length in a range of approximately ⅔ to ⅘ of the length of needle body 758, and can have a thickness in a range of approximately 3-200 μm.

In various embodiments, insulation layer 765 and insulation layer 766 can be formed by coating. In one embodiment, insulation layer 765 and insulation layer 766 are formed in the same coating process. In other words, insulation layer 765 extends to a portion of handle 766. The coating can be applied using a standard industry procedure. For example, the needles are first cleaned with alcohol and then put on low energy plasma to improve adhesion. After masking the area that is not to be coated, a thin layer of the coating is applied via chemical vapor deposition at room temperature. In various embodiments, insulation layer 765 is formed by coating using an electrically non-conductive material that is non-toxic and biocompatible. The resulting insulation layer 765 can sustain acupunctural maneuvers and a sterilization procedure. Examples of such electrically non-conductive material can include electrically non-conductive polymers, such as Parylene (by Diamond-MT, Johnstown, Pa.). In various embodiments, insulation layer 765 is formed by coating using a thermally non-conductive material that is non-toxic and biocompatible. The resulting nsulation layer 765 can sustain acupunctural maneuvers and a sterilization procedure. Examples of such thermally non-conductive material can include polyacrylonitrile (PAN) and polymide. In various embodiments, insulation layer 765 is formed by coating using a diffusible chemical material that is non-toxic and biocompatible. The resulting insulation layer 765 can sustain acupunctural maneuvers and a sterilization procedure. Examples of such thermally non-conductive material can include drugs, such as antibiotic and/or anti-inflammatory agents.

In various embodiments, insulation layer 765 can be formed by multi-layer coating using different coating materials. For example, insulation layer 765 can be formed by (1) coating the electrically non-conductive material over needle body 661 and then coating the thermally non-conductive material over the electrically non-conductive material, (2) coating the thermally non-conductive material over needle body 661 and then coating the electrically non-conductive material over the thermally non-conductive material, (3) coating the electrically non-conductive material over needle body 661 and then coating the diffusible chemical material over the electrically non-conductive material, (4) coating the thermally non-conductive material over needle body 661 and then coating the diffusible chemical material over the thermally non-conductive material, (5) coating the electrically non-conductive material over needle body 661, coating the thermally non-conductive material over the electrically non-conductive material, and then coating the diffusible chemical material over the thermally non-conductive material, and (6) coating the thermally non-conductive material over needle body 661, coating the electrically non-conductive material over the thermally non-conductive material and then coating the diffusible chemical material over the electrically non-conductive material. In various embodiments, such multi-layer coating can be applied to form both insulation layer 765 and insulation layer 766.

Figure 8:
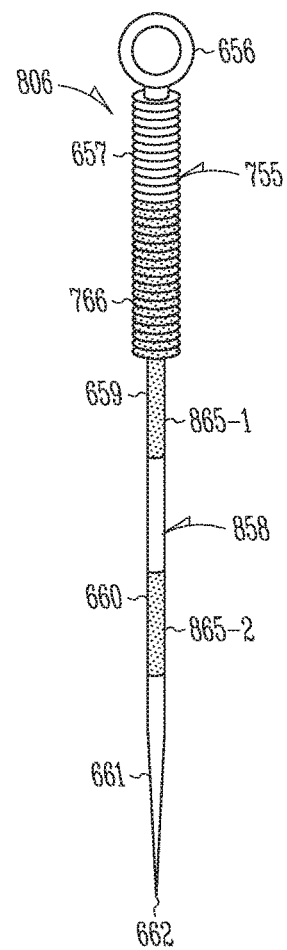
FIG. 8 is an illustration of another embodiment of a partially insulated acupuncture needle.

FIG. 8 is an illustration of another embodiment of a partially insulated acupuncture needle 806, which represents another example of an electrode such as one of electrode(s) 106. Acupuncture needle 806 is substantially identical or similar to acupuncture needle 706, but include a needle body 858 with two segments covered by insulation layers 865-1 and 865-2. Insulation layers 865-1 and 865-2 can be formed using the same coating process that is used to form insulation layer 765. In various embodiments, layers 865-1 and 865-2 can have a total length in a range of approximately ⅔ to ⅘ of the length of needle body 758, and can each have a thickness in a range of approximately 3-200 μm.

While acupuncture needles 706 and 806 are illustrated as examples, in various embodiments, a partially insulated acupuncture needle according to the present subject matter can include one segment of the insulation layer over a substantial portion of the needle body, or a plurality of segments of the insulation layer over a substantial portion of the needle body with each segment of the insulation layer separated from one or more other segments of the insulation layer by an non-insulated portion of the needle body. The insulation layer with one or more segments can have a total length in a range of approximately ⅔ to ⅘ of the length of the needle body.

Figure 9:
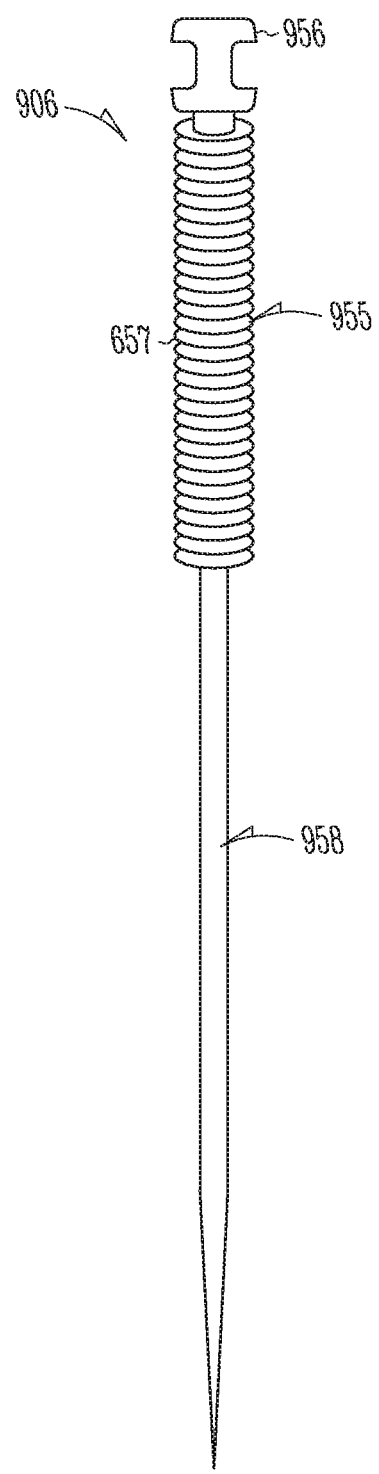
FIG. 9 is an illustration of an embodiment of an acupuncture needle including an electrical connector.

FIG. 9 is an illustration of an embodiment of an acupuncture needle 906, which represents another example of an electrode such as one of electrode(s) 106. Acupuncture needle 906 includes a handle 955 and a needle body 958. Handle 955 includes an electrical connector 956 that is custom shaped and sized to mate with a custom shaped and sized electrode connector. In one embodiment, the electrical connector 956 that is custom shaped and sized to be attached to a medical device such as IOD 405 via electrode connector 440, which can be custom shaped and sized to mate with electrical connector 956. In various embodiments, needle body 958 can be substantially identical or similar to needle body 658, 758, or 858. That is, needle body 958 can be non-insulated or partially insulated with one or more segments of insulation layer.

Figure 10:
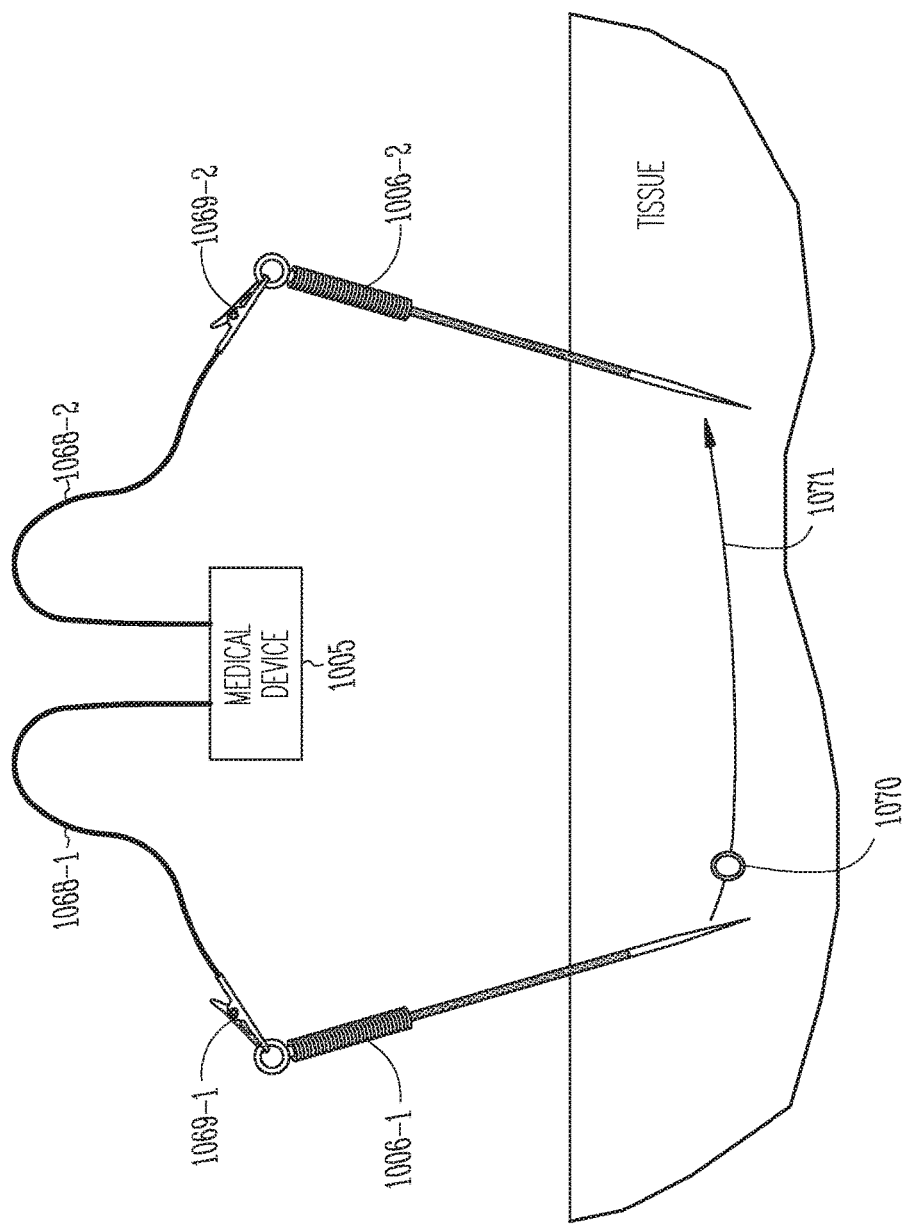
FIG. 10 is an illustration of an embodiment of acupuncture needles connected to a medical device, such as the IOD of FIG. 1 or 4, and inserted in tissue.

FIG. 10 is an illustration of an embodiment of acupuncture needles 1006 connected to a medical device 1005, such as an IOD of IOD(s) 105, and inserted in tissue. Acupuncture needles 1006-1 and 1006-2 can each be one of acupuncture needle 606, 706, 806, or 906, and electrically connected to medical device 1005 via an electrode connector 1069-1 with a cable 1068-1 and an electrode connector 1069-2 with a cable 1068-2, respectively.

In the illustrated embodiment, acupuncture needle 1006-1 is inserted into the tissue with the non-insulated portion of its needle body placed adjacent an intended target 1070 for sensing from and/or delivering stimulation to that target. When compared to uninsulated acupuncture needles, use of two partially insulated acupuncture needles 1006-1 and 1006-2 allows a current 1071 flowing between them to be more focused on intended target 1070, thereby providing for a better signal-to-noise ratio for sensing, a better energy efficiency for stimulation, and/or reduced side effects related to stimulation of unintended areas in the tissue. This can significantly reduce the risk to the patient when delivering stimulation to sites in sensitive areas of the patient's body. For example, when such sites are near the patient's heart, a current spread to unintended areas may cause the heart to beat irregularly, and when such sites are in or near the spinal cord, a current spread to unintended areas may cause nerve fibers in or around the spinal cord to respond erroneously. Thus, the use of partially insulated acupuncture needles may reduce the risk of performing electro-acupuncture in acupoints that are known to be risky if not accurately targeted.

Various embodiments can use a variety of configurations for electro-acupuncture that employ one or more partially-insulated needles as discussed in this document. Such configurations can use partially-insulated needles with same or different coating patterns, or partially-insulated and non-insulated acupuncture needles. It is desirable to place a partially-insulated acupuncture needle with its non-insulated portion adjacent the target site. Thus, in various embodiments, partially-insulated acupuncture needles with different sizes and different coating patterns can be provided to allow the user to choose an approximately optimal acupuncture needle for the target site of a certain depth under the skin. In various embodiments, the sensing capability of system 100 may facilitate such identification of the approximately optimal acupuncture needle.

Figure 11:
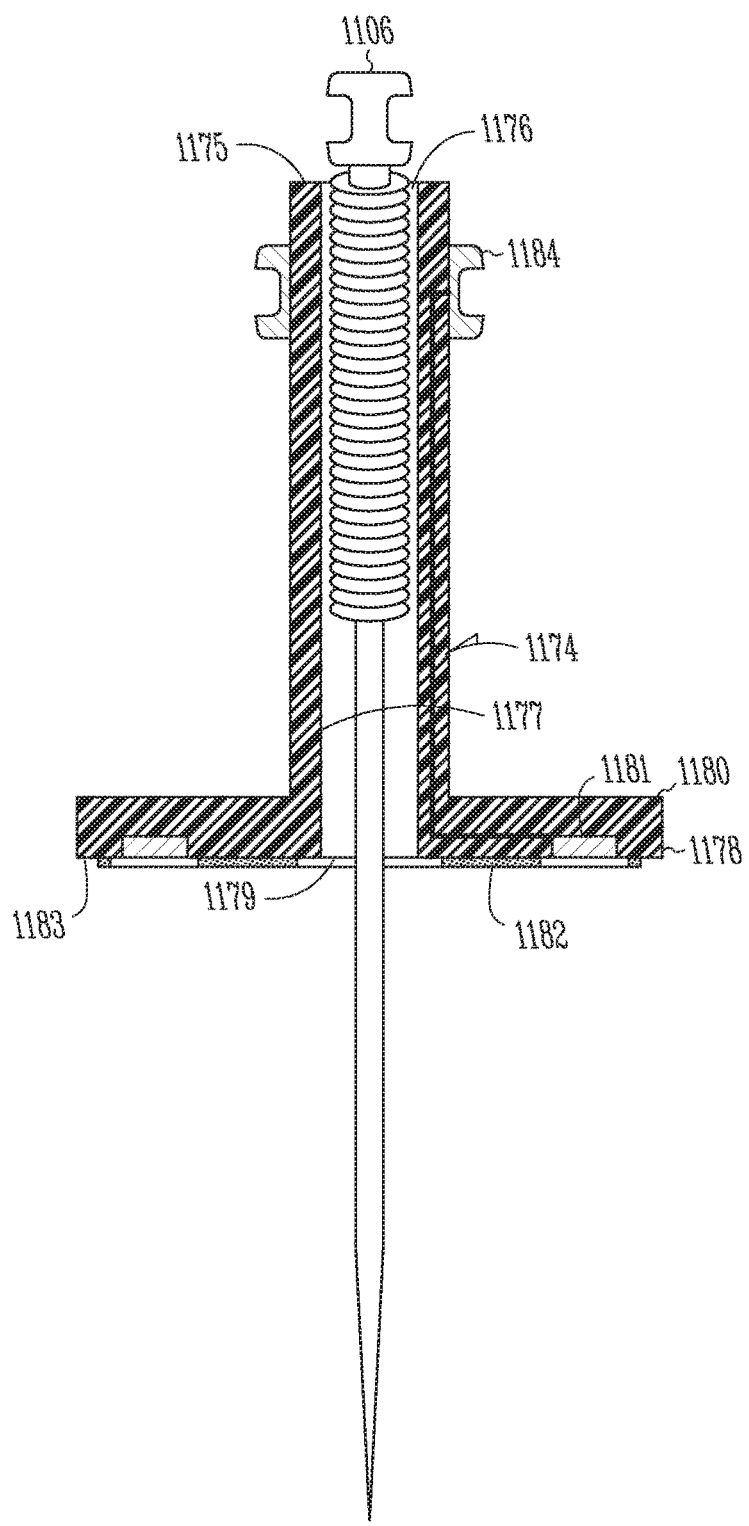
FIG. 11 is an illustration of an embodiment of an acupuncture needle and a guiding tube with an electrode.

FIG. 11 is an illustration of an embodiment of an acupuncture needle 1106 and a guiding tube 1174. Acupuncture needle 1106 can represent any one of acupuncture needles 606, 706, 806, and 906. Guiding tube 1174 (shown in a cross-sectional view) can be used to assist insertion of acupuncture needle 1106 into tissue of the patient, and can function as a needle stopper that stops further insertion of acupuncture needle 1106 when its handle is entirely or substantially inside guiding tube 1174.

In various embodiments, guiding tube 1174 can be an elongate tube made of an electrically non-conductive material that is substantially stiff. The elongate tube includes a proximal end 1175 including a proximal opening 1176, a distal end 1178 including a distal opening 1179, and a lumen 1177 between proximal opening 1176 and distal opening 1179 to allow the needle tip of acupuncture needle 1106 to enter proximal opening 1176 and exit from distal opening 1179. Distal end 1178 is to contact the skin in a site where acupuncture needle 1106 is to be inserted into the patient's tissue. In various embodiments, an electrode is incorporated into distal end 1178. In the illustrated embodiment, distal end 1178 includes a disk 1180 that includes a skin-contact surface 1183, and a ring-shaped electrode 1181 is incorporated onto skin-contact surface 1183. In one embodiment, an adhesive material 1182 is applied to skin-contact surface 1183, such as adjacent to electrode 1181, to allow disk 1180 to be stably attached onto the skin. In various embodiments, disk 1180 can include one or more electrodes of any suitable shape(s) incorporated onto skin-contact surface 1183. Guiding tube 1174 includes an electrical connector 1184 that is electrically connected to electrode 1181 and allow for electrical connection to one of IOD(s) 105 directly or via a cable.

Figure 12:
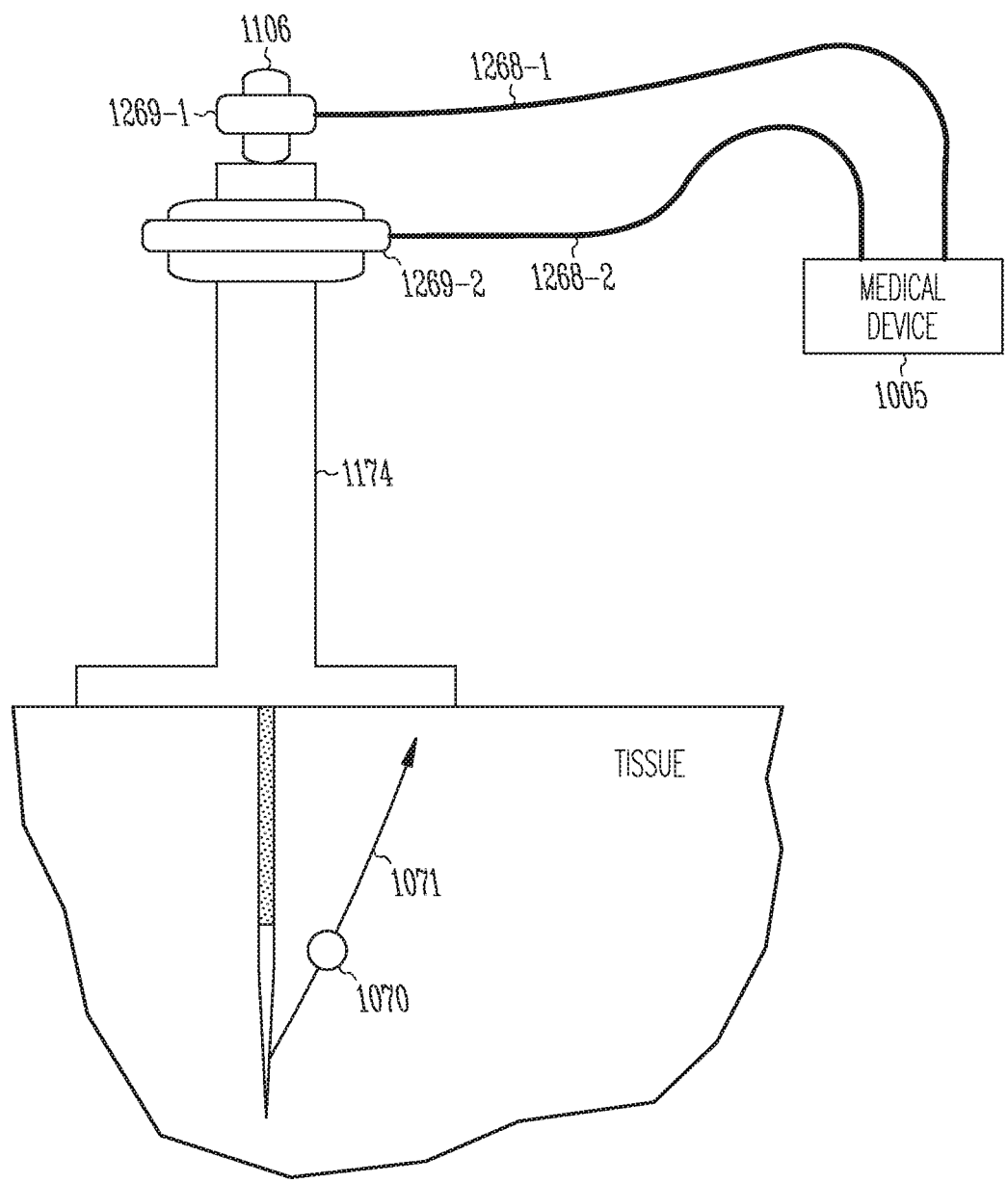
FIG. 12 is an illustration of an embodiment of the acupuncture needle and the guiding tube of FIG. 11 connected to a medical device, such as the IOD of FIG. 1 or 4, and inserted into tissue.

FIG. 12 is an illustration of an embodiment of acupuncture needle 1106 and guiding tube 1174 connected to medical device 1105 and inserted into the patient's tissue. The needle body of acupuncture needle 1106 and electrode 1181 of guiding tube 1174 are electrically connected to medical device 1005 via an electrode connector 1269-1 with a cable 1268-1 and an electrode connector 1269-2 with a cable 1268-2, respectively. As illustrated in FIG. 12, acupuncture needle 1106 and guiding tube 1174 provides a pair of electrodes needed to sense a signal from and/or deliver stimulation to target 1070, thereby eliminating the need for another acupuncture needle. Using a partially insulated acupuncture needle for acupuncture needle 1106 can provide the same advantages over using a non-insulated acupuncture needle as discussed above with reference to FIG. 10.

Figure 13:
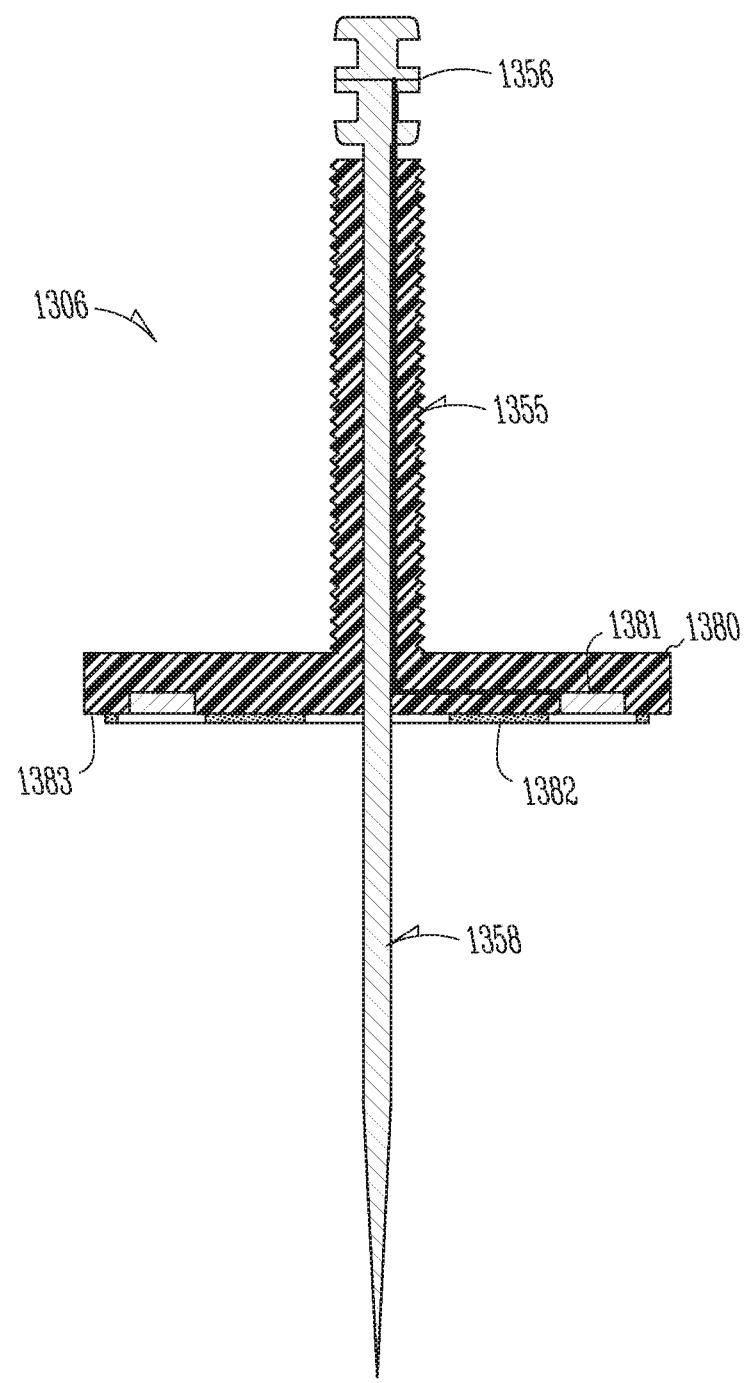
FIG. 13 is an illustration of an embodiment of an acupuncture needle including a needle stopper with an electrode.

FIG. 13 is an illustration of an embodiment of an acupuncture needle 1306 (shown in cross-sectional view) that includes a handle 1355 and a needle body 1358. In various embodiments, needle body 1358 can be substantially identical or similar to needle body 658, 758, or 858. That is, needle body 1358 can be non-insulated or partially insulated with one or more segments of insulation layer. Acupuncture needle 1306 includes a disk 1380 coupled between handle 1355 and needle body 1358. In various embodiments, disk 1380 can be made of an electrically non-conductive material, and can be used to prevent needle body 1358 from over insertion into the patient's tissue. That is, disk 1380 can function as a needle stopper to stop advance of the needle tip of needle body 1358 in the tissue such that the needle tip is inserted to an intended depth. Disk 1380 includes a skin-contact surface 1383 that is in contact with the skin at the insertion site when acupuncture needle 1306 is fully inserted. In the illustrated embodiment, a ring-shaped electrode 1381 is incorporated onto skin-contact surface 1383. In one embodiment, an adhesive material 1382 is applied to skin-contact surface 1383, such as adjacent to electrode 1381, to allow disk 1380 to be stably attached onto the skin. In various embodiments, disk 1380 can include one or more electrodes of any suitable shape(s) incorporated onto skin-contact surface 1383. Handle 1355 includes an electrode connector 1356 that includes two connector portions that are insulated from each other. One of the two connector portions is electrically connected to needle body 1358, or electrically connected to needle body 1358 and handle 1355. The other of the two connector portions is electrically connected to electrode 1381. Electrode connector 1356 allow for separate electrical connections between needle body 1358 and one of IOD(s) 105 and between electrode 1381 and that IOD.

Figure 14:
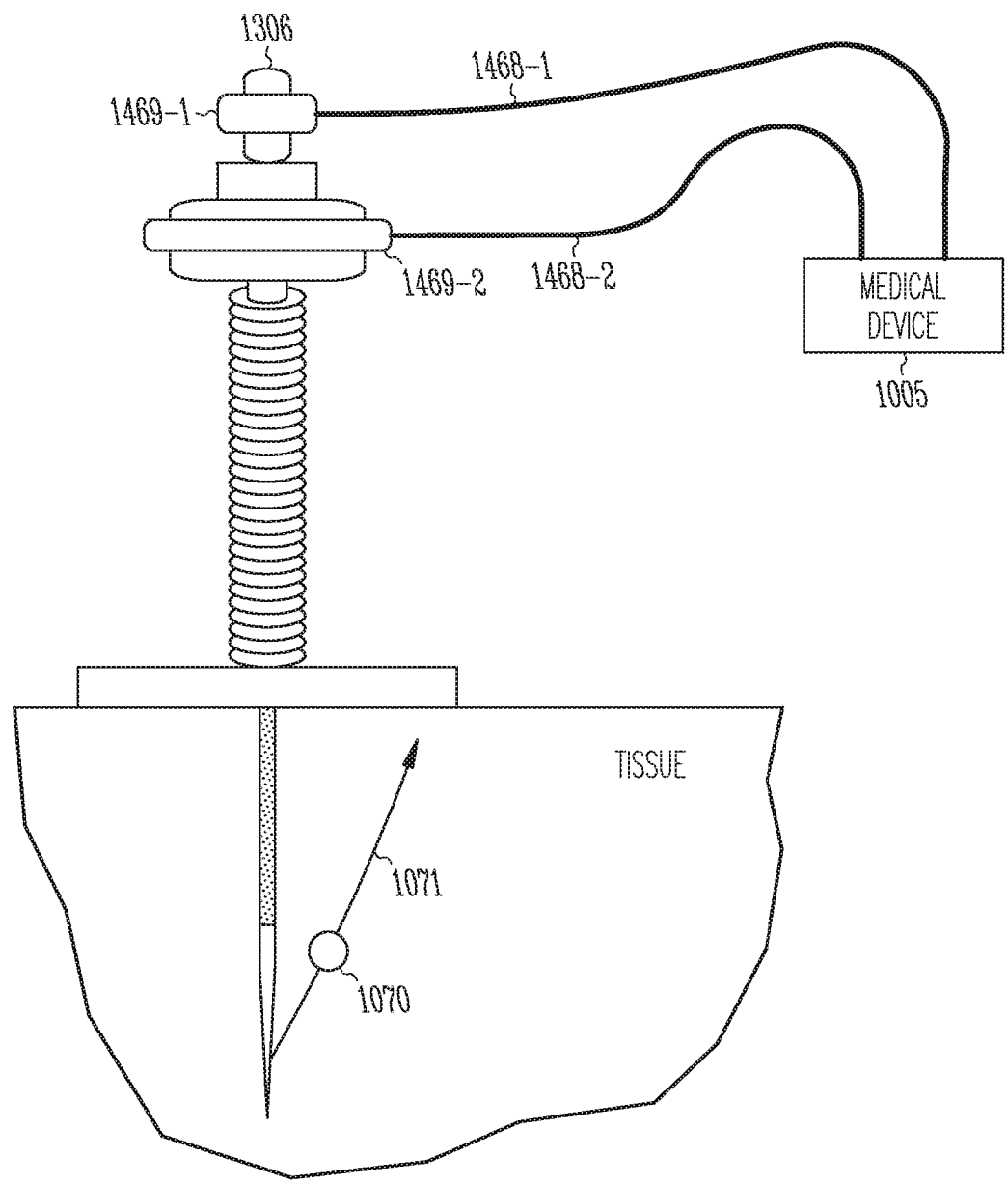
FIG. 14 is an illustration of an embodiment of the acupuncture needle of FIG. 13 connected to a medical device, such as the IOD of FIG. 1 or 4, and inserted into tissue.

FIG. 14 is an illustration of an embodiment of acupuncture needle 1306 connected to medical device 1105 and inserted into the patient's tissue. Needle body 1358 and electrode 1381 are electrically connected to medical device 1005 via an electrode connector 1469-1 with a cable 1468-1 and an electrode connector 1469-2 with a cable 1468-2, respectively. As illustrated in FIG. 14, acupuncture needle 1306 provides a pair of electrodes needed to sense a signal from and/or deliver stimulation to target 1070, thereby eliminating the need for another acupuncture needle. Using a partially insulated acupuncture needle for acupuncture needle 1306 can provide the same advantages over using a non-insulated acupuncture needle as discussed above with reference to FIG. 10.

Some non-limiting examples of apparatuses and methods according to the present subject matter are provided as follows.

In Example 1, an apparatus configured to provide an interface between a medical device and a person includes an acupuncture needle configured to be connected to the medical device. The acupuncture needle may include a handle, a needle body coupled to the handle, and an insulation layer. The handle and the needle body may be substantially bendable and have sufficient stiffness for percutaneous insertion of a substantial portion of the needle body into the tissue of the person by applying force using the handle, and the needle tip is shaped and sized to pierce the skin and the tissue of the person. The needle body may include a proximal end portion connected to the handle, a distal end portion including a needle tip, and an elongate body shaft coupled between the proximal end portion and the distal end portion. The insulation layer may be over at least a portion of the needle body such that the needle body includes at least one insulated portion and at least one non-insulated portion. The insulation layer may be electrically nonconductive.

In Example 2, the subject matter of Example 1 may optionally be configured such that the handle includes a connector electrically coupled to the needle body to allow for an electrical connection between the needle body and the medical device.

In Example 3, the subject matter of Example 2 may optionally be configured such that the connector is configured to allow the acupuncture needle to be attached to the medical device directly.

In Example 4, the subject matter of any one or any combination of Examples 1 to 3 may optionally be configured such that the handle includes an identification feature allowing for identification of the acupuncture needle from a plurality of acupuncture needles.

In Example 5, the subject matter of any one or any combination of Examples 1 to 4 may optionally be configured such that the insulation layer includes a plurality of segments over a substantial portion of the needle body. Each segment of the plurality of segments is separated from one or more other segments of the plurality of segments by a non-insulated portion of the at least one non-insulated portion of the needle body.

In Example 6, the subject matter of any one or any combination of Examples 1 to 5 may optionally be configured such that the insulation layer extends to a portion of the handle.

In Example 7, the subject matter of any one or any combination of Examples 1 to 6 may optionally be configured such that the insulation layer is formed by coating an insulation material onto the portion of the needle body. The insulation material is biocompatible, capable of sustaining acupunctural maneuvers, and capable of sustaining sterilization of the acupuncture needle.

In Example 8, the subject matter of any one or any combination of Examples 1 to 7 may optionally be configured such that the insulation layer has a length in a range of approximately ⅔ to ⅘ of the length of the needle body and a thickness in a range of approximately 3-200 μm.

In Example 9, the subject matter of any one or any combination of Examples 7 and 8 may optionally be configured such that the insulation layer is formed by multiple layers of coating using two or more different coating materials each selected for one layer of the multiple layers.

In Example 10, the subject matter of Example 9 may optionally be configured such that the two or more different coating materials include an electrically nonconductive material and one or more of a thermally nonconductive material and a diffusible chemical material that is electrically non-conductive.

In Example 11, a method for providing an interface between a medical device and a person is provided. The method may include providing an acupuncture needle including a handle, a needle body coupled to the handle and including a proximal end portion connected to the handle, a distal end portion including a needle tip, and an elongate body shaft coupled between the proximal end portion and the distal end portion, and forming an insulation layer over at least a portion of the needle body such that the needle body includes at least one insulated portion and at least one non-insulated portion, the insulation layer being electrically non-conductive. The handle and the needle body are substantially bendable and have sufficient stiffness for percutaneous insertion of a substantial portion of the needle body into the tissue of the person by applying force using the handle, and the needle tip is shaped and sized to pierce the skin and the tissue of the person.

In Example 12, the subject matter of Example 11 may optionally include sensing a signal from the person using the medical device via the at least one non-insulated portion of the needle body.

In Example 13, the subject matter of any one or any combination of Examples 11 and 12 may optionally include delivering a stimulus from the medical device to the tissue via the at least one non-insulated portion of the needle body.

In Example 14, the subject matter of any one or any combination of Examples 11 to 13 may optionally include providing the handle of the acupuncture needle with a connector electrically coupled to the needle body to allow for an electrical connection between the needle body and the medical device.

In Example 15, the subject matter of Example 14 may optionally include attaching the acupuncture needle to the medical device directly via the connector.

In Example 16, the subject matter of forming the insulation layer over at least the portion of the needle body as found in any one or any combination of Examples 11 to 15 may optionally include forming the insulation layer including a plurality of segments over a substantial portion of the needle body, each segment of the plurality of segments separated from one or more other segments of the plurality of segments by a non-insulated portion of the at least one non-insulated portion of the needle body.

In Example 17, the subject matter of forming the insulation layer over at least the portion of the needle body as found in any one or any combination of Examples 11 to 16 may optionally include coating an insulation material onto the portion of the needle body, the insulation material being biocompatible, capable of sustaining acupunctural maneuvers, and capable of sustaining sterilization of the acupuncture needle.

In Example 18, the subject matter of any one or any combination of Examples 11 to 17 may optionally include forming another insulation layer over at least a portion of the handle.

In Example 19, the subject matter of coating the insulation material onto the portion of the needle body as found in any one or any combination of Examples 17 and 18 may optionally include coating at least a layer of an electrically non-conductive and one or more layers of one or more of a thermally non-conductive material and a diffusible chemical material over the portion of the needle body.

In Example 20, the subject matter of any one or any combination of Examples 11 to 19 may optionally include providing the acupuncture needle with a unique identification feature to allow for identification of the acupuncture needle from a set of acupuncture needles.

In Example 21, an apparatus configured to provide an interface between a medical device and a person may include an acupuncture needle and a guiding tube. The acupuncture needle may be configured to be connected to the medical device, and may include a handle and a needle body coupled to the handle. The needle body includes a proximal end portion connected to the handle, a distal end portion including a needle tip suitable for piercing the skin and the tissue, and an elongate body shaft coupled between the proximal end portion and the distal end portion. The guiding tube may be configured to assist percutaneous insertion of a substantial portion of the needle body into the tissue of the person, and may include a proximal end including a proximal opening, a distal end including a distal opening for contacting skin, a lumen between the proximal opening and the distal opening, the lumen configured to allow the needle tip to enter the proximal opening and exit from the distal opening, an electrode incorporated into the distal end, and a connector configured to allow for electrical connection between the electrode and the medical device.

In Example 22, the subject matter of Example 21 may optionally be configured such that the distal end of the guiding tube includes a disk including a skin-contact surface configured to be in contact with the skin when the substantial portion of the needle body is being inserted into the tissue, and the electrode is incorporated onto the skin-contact surface of the disk.

In Example 23, the subject matter of Example 22 may optionally be configured such that the guiding tube includes an adhesive material incorporated onto one or more portions of the disk to stably attach the guiding tube onto the skin.

In Example 24, the subject matter of any one or any combination of Examples 21 to 23 may optionally be configured such that the handle and the needle body of the acupuncture needle are substantially bendable and have sufficient stiffness for percutaneous insertion into the tissue by applying force using the handle.

In Example 25, the subject matter of any one or any combination of Examples 21 to 24 may optionally be configured such that the acupuncture needle includes an insulation layer over at least a portion of the needle body such that the needle body includes one or more insulated portions and one or more non-insulated portions, the insulation layer being electrically nonconductive.

In Example 26, the subject matter Example 25 may optionally be configured such that the insulation layer is formed by coating an insulation material onto the portion of the needle body. The insulation material is biocompatible, capable of sustaining acupunctural maneuvers, and capable of sustaining sterilization of the acupuncture needle.

In Example 27, an apparatus configured to provide an interface between a medical device and a person may include an acupuncture needle configured to be connected to the medical device. The acupuncture needle may include a handle, a needle body coupled to the handle, a disk coupled between the handle and the needle body, and an electrode. The needle body may include a proximal end portion connected to the handle, a distal end portion including a needle tip suitable for piercing the skin and the tissue, and an elongate body shaft coupled between the proximal end portion and the distal end portion. The disk may be coupled between the handle and the needle body and approximately perpendicular to the handle and the needle body. The disk may including a skin-contact surface configured to be in contact with the skin of the person when a portion of the needle body is inserted into the tissue of the person such that the needle tip is at an intended depth. The electrode may be incorporated onto the skin-contact surface of the disk.

In Example 28, the subject matter Example 27 may optionally be configured such that the acupuncture needle further includes an adhesive material incorporated onto one or more portions of the skin-contact surface of the disk to stably attach the disk onto the skin.

In Example 29, the subject matter of any one or any combination of Examples 27 and 28 may optionally be configured such that the acupuncture needle includes a connector configured to allow for a first electrical connection between the needle body and the medical device and a second electrical connection between the electrode and the medical device.

In Example 30, the subject matter of any one or any combination of Examples 27 to 29 may optionally be configured such that the handle and the needle body of the acupuncture needle are substantially bendable and have sufficient stiffness for percutaneous insertion of the portion of the needle body into the tissue the tissue by applying force using the handle.

In Example 31, the subject matter of any one or any combination of Examples 27 to 30 may optionally be configured such that the acupuncture needle further comprises an insulation layer over at least a portion of the needle body such that the needle body includes one or more insulated portions and one or more non-insulated portions. The insulation layer is electrically nonconductive.

In Example 32, the subject matter of Example 31 may optionally be configured such that the insulation layer is formed by coating an insulation material onto the portion of the needle body, the insulation material being biocompatible, capable of sustaining acupunctural maneuvers, and capable of sustaining sterilization of the acupuncture needle.

In Example 33, a method for providing an interface between a medical device and a person is provided. The method may include providing an acupuncture needle including a handle and a needle body coupled to the handle. The needle body may include a proximal end portion connected to the handle, a distal end portion including a needle tip, and an elongate body shaft coupled between the proximal end portion and the distal end portion. The handle and the needle body may be substantially bendable and have sufficient stiffness for percutaneous insertion of a substantial portion of the needle body into the tissue by applying force using the handle. The needle tip may be shaped and sized to pierce the skin and the tissue. The method may further include providing a needle stopper configured to stop the needle tip from further penetration into the tissue when an intended depth is reached. The needle stopper may include a skin-contact surface that contacts the skin when the needle tip is at the intended depth. The method may further include incorporating an electrode onto the skin-contact surface, providing a first electrical connection between the needle body and the medical device, and providing a second electrical connection between the electrode and the medical device.

In Example 34, the subject matter of providing the needle stopper as found in Example 33 may optionally include providing a guiding tube including a proximal end including a proximal opening, a distal end including a distal opening and a disk including the skin-contact surface, a lumen between the proximal opening and the distal opening, the lumen configured to allow the needle tip to enter the proximal opening and exit from the distal opening.

In Example 35, the subject matter of providing the needle stopper as found in Example 33 may optionally include incorporating a disk into the acupuncture needle between the handle and the needle. The disk includes the skin-contact surface.

In Example 36, the subject matter of any one or any combination of Examples 33 to 35 may optionally include forming an insulation layer over at least a portion of the needle body of the acupuncture needle such that the needle body includes one or more insulated portions and one or more non-insulated portions. The insulation layer is electrically nonconductive.

In Example 37, the subject matter of forming the insulation layer over at least the portion of the needle body as found in Example 36 may optionally include coating an insulation material onto the portion of the needle body, the insulation material being biocompatible, capable of sustaining acupunctural maneuvers, and capable of sustaining sterilization of the acupuncture needle.

In Example 38, the subject matter of coating the insulation material onto the portion of the needle body as found in Example 37 may optionally include coating one or more of an electrically non-conductive material and a thermally non-conductive material onto the portion of the needle body.

In Example 39, the subject matter of coating the insulation material onto the portion of the needle body as found in Example 38 may optionally include coating a diffusible chemical material onto the coated one or more of the electrically non-conductive material and the thermally non-conductive material.

In Example 40, the subject matter of any one or any combination of Examples 33 to 39 may optionally include performing one or more of sensing a signal from the person using the medical device and delivering a stimulus from the medical device to the tissue via one or more of the at least one non-insulated portion of the needle body and the electrode incorporated onto the skin-contact surface of the needle stopper.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An apparatus configured to provide an interface between a medical device and a person having skin and tissue under the skin, the apparatus comprising:
    an acupuncture needle configured to be connected to the medical device, the acupuncture needle including:
        a handle; and
        a needle body coupled to the handle, the needle body including a proximal end portion connected to the handle, a distal end portion including a needle tip suitable for piercing the skin and the tissue, and an elongate body shaft coupled between the proximal end portion and the distal end portion; and
    a guiding tube configured to assist percutaneous insertion of a substantial portion of the needle body into the tissue, the guiding tube including:
        an elongate tube of electrically non-conductive material, the elongate tube including a proximal end including a proximal opening, a distal end including a distal opening for contacting the skin and a lumen between the proximal opening and the distal opening, the lumen configured to allow the needle tip to enter the proximal opening and exit from the distal opening;
        an electrode incorporated into the distal end of the elongate tube; and
        a connector configured to allow for electrical connection between the electrode and the medical device.

2. The apparatus of claim 1, wherein the distal end of the elongate tube comprises a disk including a skin-contact surface configured to be in contact with the skin when the substantial portion of the needle body is being inserted into the tissue, and the electrode is incorporated onto the skin-contact surface of the disk.

3. The apparatus of claim 2, wherein the guiding tube further comprises an adhesive material incorporated onto one or more portions of the disk to stably attach the guiding tube onto the skin.

4. The apparatus of claim 1, wherein the handle and the needle body of the acupuncture needle are substantially bendable and have sufficient stiffness for percutaneous insertion into the tissue by applying force using the handle.

5. The apparatus of claim 1, wherein the acupuncture needle further comprises an insulation layer over at least a portion of the needle body such that the needle body includes one or more insulated portions and one or more non-insulated portions, the insulation layer being electrically nonconductive.

6. The apparatus of claim 5, wherein the insulation layer extends to a portion of the handle of the acupuncture needle.

7. The apparatus of claim 5, wherein the insulation layer has a length in a range of approximately ⅔ to ⅘ of the length of the needle body and a thickness in a range of approximately 3-200 μm.

8. The apparatus of claim 5, wherein the insulation layer is formed by multiple layers of coating using two or more different coating materials each selected for one layer of the multiple layers.

9. The apparatus of claim 8, wherein the two or more different coating materials comprise an electrically nonconductive material and one or more of a thermally nonconductive material and a diffusible chemical material that is electrically non-conductive.

10. The apparatus of claim 5, wherein the insulation layer is formed by coating an insulation material onto the portion of the needle body, the insulation material being biocompatible, capable of sustaining acupunctural maneuvers, and capable of sustaining sterilization of the acupuncture needle.

11. The apparatus of claim 1, wherein the handle of the acupuncture needle comprises an identification feature allowing for identification of the acupuncture needle.

12. An apparatus configured to provide an interface between a medical device and a person having skin and tissue under the skin, the apparatus comprising:
an acupuncture needle configured to be connected to the medical device, the acupuncture needle including:
a handle;
a needle body coupled to the handle, the needle body including a proximal end portion connected to the handle, a distal end portion including a needle tip suitable for piercing the skin and the tissue, and an elongate body shaft coupled between the proximal end portion and the distal end portion;
a disk coupled to the handle, positioned between the handle and the needle body, and being approximately perpendicular to the handle and the needle body, the disk made of an electrically non-conductive material and including a skin-contact surface configured to be in contact with the skin when a portion of the needle body is inserted into the tissue such that the needle tip is at an intended depth;
an electrode incorporated onto the skin-contact surface of the disk and an elongate tube of electrically non-conductive material coupled to the disk.

13. The apparatus of claim 12, wherein the acupuncture needle further comprises an adhesive material incorporated onto one or more portions of the skin-contact surface of the disk to stably attach the disk onto the skin.

14. The apparatus of claim 12, wherein the acupuncture needle further comprises a connector configured to allow for a first electrical connection between the needle body and the medical device and a second electrical connection between the electrode and the medical device.

15. The apparatus of claim 12, wherein the handle and the needle body of the acupuncture needle are substantially bendable and have sufficient stiffness for percutaneous insertion of the portion of the needle body into the tissue the tissue by applying force using the handle.

16. The apparatus of claim 12, wherein the acupuncture needle further comprises an insulation layer over at least a portion of the needle body such that the needle body includes one or more insulated portions and one or more non-insulated portions, the insulation layer being electrically nonconductive.

17. The apparatus of claim 16, wherein the insulation layer has a length in a range of approximately ⅔ to ⅘ of the length of the needle body and a thickness in a range of approximately 3-200 μm.

18. The apparatus of claim 16, wherein the insulation layer is formed by multiple layers of coating using two or more different coating materials each selected for one layer of the multiple layers.

19. The apparatus of claim 18, wherein the two or more different coating materials comprise an electrically nonconductive material and one or more of a thermally nonconductive material and a diffusible chemical material that is electrically non-conductive.

20. The apparatus of claim 16, wherein the insulation layer is formed by coating an insulation material onto the portion of the needle body, the insulation material being biocompatible, capable of sustaining acupunctural maneuvers, and capable of sustaining sterilization of the acupuncture needle.

* * * * *